US010455831B2

(12) United States Patent
Chason et al.

(10) Patent No.: US 10,455,831 B2
(45) Date of Patent: Oct. 29, 2019

(54) LIQUID MATERIAL SYSTEMS WITH MULTIFUNCTIONAL ORGANOMETALLIC ADDITIVES (71) Applicant: DMR INTERNATIONAL, INC., Woodstock, IL (US)

(72) Inventors: Marc Chason, Schaumburg, IL (US); Daniel Roman Gamota, Palatine, IL (US); Rick Latella, Woodstock, IL (US)

(73) Assignee: DMR International, Inc., Woodstock, IL (US)

( * ) Notice: Subject to any disclaimer, the term of this patent is extended or adjusted under 35 U.S.C. 154(b) by 452 days.

(21) Appl. No.: 14/277,112

(22) Filed: May 14, 2014

(65) Prior Publication Data

US 2014/0271760 A1   Sep. 18, 2014

Related U.S. Application Data (63) Continuation-in-part of application No. 13/833,689, filed on Mar. 15, 2013, now Pat. No. 9,138,000, and a continuation-in-part of application No. 13/833,581, filed on Mar. 15, 2013, and a continuation-in-part of application No. 13/833,445, filed on Mar. 15, 2013, now Pat. No. 9,795,141.

(60) Provisional application No. 61/823,198, filed on May 14, 2013.

(51) Int. Cl.
| *A01N 55/02* | (2006.01) |
| *A01N 37/02* | (2006.01) |
| *A01N 59/16* | (2006.01) |
| *A01N 59/20* | (2006.01) |

(52) U.S. Cl.
CPC ............ *A01N 37/02* (2013.01); *A01N 59/16* (2013.01); *A01N 59/20* (2013.01)

(58) Field of Classification Search
CPC .................................................... A01N 37/02
See application file for complete search history.

(56) References Cited

U.S. PATENT DOCUMENTS

| 3,590,000 | A | 6/1971 | Palermiti |
| 4,428,989 | A | 1/1984 | Marshall |
| 5,439,957 | A | 8/1995 | Takimoto et al. |
| 7,022,750 | B2 | 4/2006 | Camp et al. |
| 7,354,596 | B1 | 4/2008 | Banovetz et al. |
| 7,595,355 | B2 | 9/2009 | Trogolo |
| 8,124,169 | B2 | 2/2012 | Ylitalo et al. |
| 8,470,755 | B1* | 6/2013 | Tajmamet .............. A01N 59/16 |
| | | | 510/235 |
| 2005/0238602 | A1* | 10/2005 | Modak et al. ............. 424/70.11 |
| 2006/0188551 | A1 | 8/2006 | Hauser et al. |
| 2008/0317800 | A1 | 12/2008 | Amirzadeh-Asl |
| 2009/0093577 | A1 | 4/2009 | Bernard et al. |
| 2009/0130157 | A1 | 5/2009 | Ylitalo et al. |
| 2009/0186064 | A1 | 7/2009 | Szycher |
| 2009/0201759 | A1 | 8/2009 | Mills |
| 2010/0204357 | A1 | 8/2010 | Chasser et al. |
| 2010/0330142 | A1 | 12/2010 | Falk et al. |
| 2011/0002872 | A1 | 1/2011 | Ohashi et al. |
| 2012/0272967 | A1 | 11/2012 | Stewart et al. |

FOREIGN PATENT DOCUMENTS

| CN | 101481571 | * | 1/2009 |
| EP | 0290095 | A1 | 11/1988 |
| GB | 709575 | | 10/1951 |
| JP | 1995-018879 | * | 11/1994 |
| WO | 01/32138 | A1 | 5/2001 |
| WO | 2005061022 | A2 | 7/2005 |
| WO | 2011/088205 | A1 | 7/2011 |
| WO | 2012091407 | A2 | 7/2012 |
| WO | 2012/158702 | A1 | 11/2012 |
| WO | 2012158702 | A2 | 11/2012 |

OTHER PUBLICATIONS

Office Action received in U.S. Appl. No. 13/833,581 dated Sep. 3, 2014.
Notification, Search Report and Written Opinion received in PCT Application No. PCT/IB2015/052560 dated Jun. 22, 2015.
Office Action received in U.S. Appl. No. 13/833,689 dated Jun. 5, 2014.
Office Action received in U.S. Appl. No. 13/833,445 dated Jul. 7, 2014.
Office Action received in U.S. Appl. No. 13/833,689 dated Aug. 19, 2014.
International Search Report dated Apr. 25, 2014 in corresponding International Patent Application No. PCT/IB2014/058130.
International Search Report dated May 19, 2014 in corresponding International Patent Application No. PCT/IB2014/058127.
Office Action dated Sep. 12, 2016 in corresponding U.S. Appl. No. 13/833,581.

* cited by examiner

*Primary Examiner* — David J Blanchard
*Assistant Examiner* — Sarah Alawadi
(74) *Attorney, Agent, or Firm* — Miles & Stockbridge P.C.; Ajay A. Jagtiani (57) ABSTRACT

Described are antimicrobial liquid products comprising one or more antimicrobial organometallic additives dispersed throughout an organic host liquid.

47 Claims, 3 Drawing Sheets

LIQUID MATERIAL SYSTEMS WITH MULTIFUNCTIONAL ORGANOMETALLIC ADDITIVES

CROSS-REFERENCE TO RELATED APPLICATIONS

This application claims benefit of priority to U.S. Provisional Patent Application No. 61/823,198 to Chason et al., entitled "LIQUID MATERIAL SYSTEMS WITH MULTIFUNCTIONAL ORGANO-METALLIC ADDITIVES," filed May 14, 2013, U.S. patent application Ser. No. 13/833,689 to Chason et al., entitled "ANTIMICROBIAL POLYMER SYSTEMS USING MULTIFUNCTIONAL ORGANOMETALLIC ADDITIVES FOR WAX HOSTS," filed Mar. 15, 2013, of which the present application is a continuation-in-part, U.S. patent application Ser. No. 13/833,581 to Chason et al., entitled "ANTIMICROBIAL POLYMER SYSTEMS USING MULTIFUNCTIONAL ORGANOMETALLIC ADDITIVES FOR THERMOSET HOSTS," filed Mar. 15, 2013, of which the present application is a continuation-in-part, and U.S. patent application Ser. No. 13/833,445 to Chason et al., entitled "ANTIMICROBIAL POLYMER SYSTEMS USING MULTIFUNCTIONAL ORGANOMETALLIC ADDITIVES FOR POLYURETHANE HOSTS," filed Mar. 15, 2013, of which the present application is a continuation-in-part."

All of the above patents and patent applications are incorporated herein by reference in their entirety.

BACKGROUND

Field of the Invention

The present invention relates to antimicrobial polymer systems.

Related Art

Material surfaces may become contaminated with disease-causing agents. For example, used in aqueous environments or environments where moisture resides, microbes may be transferred to the surface of the metal products, organic products, inorganic products, polymer products, etc.

SUMMARY

According to a first broad aspect, the present invention provides a product comprising: an inorganic liquid, and a dispersed liquid material system comprising: an organic host liquid dispersed throughout the inorganic liquid, and one or more antimicrobial organometallic additives dispersed throughout the organic host liquid, wherein each of the one or more antimicrobial organometallic additives is water insoluble or sparingly soluble in water and comprises a long-chain fatty acid group, and wherein the organic host liquid is a liquid at room temperature.

According to a second broad aspect, the present invention provides a method comprising the following step: (a) dispersing a liquid material system in an inorganic liquid to thereby form a dispersed liquid material product comprising a dispersed liquid material system dispersed in the inorganic liquid, wherein the dispersed liquid material system comprises an organic host liquid, wherein one or more antimicrobial organometallic additives are dispersed throughout the organic host liquid, wherein each of the one or more antimicrobial organometallic additives is water insoluble or sparingly soluble in water and comprises a long-chain fatty acid group, and wherein the organic host liquid is a liquid at room temperature.

According to a third broad aspect, the present invention provides a product comprising: a liquid material system comprising: an organic host liquid, and one or more antimicrobial organometallic additives dispersed throughout the organic host liquid, wherein each of the one or more antimicrobial organometallic additives is water insoluble or sparingly soluble in water and comprises a long-chain fatty acid group, and wherein the organic host liquid is a liquid at room temperature.

According to a fourth broad aspect, the present invention provides a method comprising the following step: (a) mixing one or more antimicrobial organometallic additives with an organic host liquid to thereby form a liquid material system comprising the one or more antimicrobial organometallic additives dispersed throughout the organic host liquid, wherein each of the one or more antimicrobial organometallic additives is water insoluble or sparingly soluble in water and comprises a long-chain fatty acid group, and wherein the organic host liquid is a liquid at room temperature.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention. The sizes and the relative heights, widths, diameters, thicknesses, etc. of features in the drawings are not necessarily to scale unless specifically indicated otherwise. For example, in the drawings the thickness of a coating in the drawings may be shown thicker relative to the substrate on which the coating is coated to allow for details of the components of the coating to be better illustrated. Also in the drawings, organometallic additives are shown as being much larger than these components would be in the polymer host matrix in which these components are dispersed for ease of illustration. In the drawings, the organometallic additives are depicted as circles. This is only a schematic representation as the additive form factor of the present invention may be circular, spherical, linear, branched or other form factor.

DETAILED DESCRIPTION OF THE PREFERRED EMBODIMENTS

Definitions

Where the definition of terms departs from the commonly used meaning of the term, applicant intends to utilize the definitions provided below, unless specifically indicated.

For purposes of the present invention, it should be noted that the singular forms, "a," "an," and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc. are merely used for convenience in describing the various embodiments of the present invention. The embodiments of the present invention may be oriented in various ways. For example, the diagrams, apparatuses, etc. shown in the drawing figures may be flipped over, rotated by 90° in any direction, reversed, etc.

For purposes of the present invention, a value or property is "based" on a particular value, property, the satisfaction of a condition or other factor, if that value is derived by performing a mathematical calculation or logical decision using that value, property, the satisfaction of a condition or other factor.

For purposes of the present invention, the term "additive" refers to anything dispersed in an organic host liquid. A multifunctional metal blend (MFMB) organometallic additive is an example of a type of additive.

For purposes of the present invention, the term "antimicrobial" refers to a material that kills or inhibits the growth of microorganisms such as bacteria, viruses, fungi, molds, yeasts, algae or protozoans.

For purposes of the present invention, the term "antimicrobial additive" refers to an additive that is antimicrobial.

For purposes of the present invention, the term "antimicrobial-resistant liquid" refers to a liquid that inhibits antimicrobial activity.

For purposes of the present invention, the term "antimicrobial organometallic additive" refers to an organometallic additive that imparts antimicrobial properties to a product of which the antimicrobial organometallic additive is a part or increases the antimicrobial properties of a product of which the antimicrobial organometallic additive is a part.

For purposes of the present invention, the term "degree of antimicrobial activity" refers to the percentage reduction in Colony Forming Units (CFU) observed when a polymer product is subjected to JIS Z 2801 test protocol described below in the Examples section. For example, if a 99.99831% reduction in Colony Forming Units (CFU) is observed for a polymer product, the product has a 99.99831% degree of antimicrobial activity.

For purposes of the present invention, the term "dispersed" refers to one or more additives being blended with, mixed with, dispersed in, dissolved in, distributed in, suspended in, scattered in, etc., an organic host liquid.

For purposes of the present invention, the term "dispersed liquid material product" refers to a liquid product comprising a liquid material system that is dispersed in an inorganic liquid by dispersing the organic host liquid of the liquid material system in the inorganic liquid. Together the dispersed liquid material system and the inorganic liquid form the dispersed liquid material product. A dispersed liquid material product may be used to produce a coating on a substrate such as a liquid material product film.

For purposes of the present invention, the term "dispersed liquid material system" refers to a liquid system comprising a liquid material system that is dispersed in an inorganic liquid by dispersing the organic host liquid of the liquid material system in the inorganic liquid.

For purposes of the present invention, the term "dispersed throughout" refers to one or more antimicrobial multifunctional metal blend (MFMB) organometallic additives being distributed relatively evenly throughout an organic host liquid. For purposes of the present invention, the term "dispersed throughout" also refers to any material that is distributed evenly throughout a liquid, such as organic host liquid dispersed throughout an inorganic liquid.

For purposes of the present invention, the term "organic host liquid" and the term "host liquid" refer to a liquid or a mixture of organic liquids in which one or more organometallic additives are dispersed. An organic host liquid may itself be a dispersed phase of an emulsion, i.e., the organic host liquid may be dispersed in an inorganic continuous phase such as water, ammonia, etc. In one embodiment, a host liquid is a liquid at room temperature. In some embodiments of the present invention, an organic host liquid may have an inorganic liquid dispersed therein.

For purposes of the present invention, the term "liquid material system" refers to a liquid composition comprising an organic host liquid in which there has been dispersed one or more organometallic additives. A liquid material system may comprise an emulsion in which the organic host liquid is the dispersed phase in a continuous phase that comprises an inorganic liquid such as water. In such a liquid material system, the one or more organometallic additives are dispersed in the organic host liquid and the organic host liquid is in turned dispersed in the continuous phase.

For purposes of the present invention, the term "long-chain fatty acid" refers to a fatty acid having an aliphatic tail of thirteen or more carbon atoms.

For purposes of the present invention, the term "long-chain fatty acid group" refers to the ester group derived from a long-chain fatty acid. An example of a long-chain fatty acid group is a stearate group.

For purposes of the present invention, the term "majority" refers to a majority by molar amount. For example, if there were a mixture of antimicrobial organometallic additives comprising 1.0 mole of copper stearate and 1.0 mole of silver stearate present in a liquid, 0.1 total moles of metals in a UV absorber dispersed throughout the liquid and 0.2 moles of metal ions in a color in the liquid, the antimicrobial organometallic additives would constitute a majority of the metallic species in the liquid: 2.0 total moles of antimicrobial organometallic additives to 0.3 total moles of metallic species from other sources dispersed throughout the liquid.

For purposes of the present invention, the term "metallic species" refers to the metals, metal ions and metal-containing compounds present in a liquid material system of the present invention. In addition to the metals in the metallic component of multifunctional metal blend (MFMB) organometallic additives of the present invention, liquid material systems of the present invention may also include metallic species that are metals, metal ions and metal-containing compounds such as metal salts, metal oxides, organometallic oxides, etc., that are dispersed in an organic host liquid.

For purposes of the present invention, the term "multifunctional metal blend (MFMB)" refers to an antimicrobial organometallic additive having antimicrobial properties or a mixture of organometallic additives having antimicrobial properties. Each antimicrobial organometallic additive of an MFMB has a metallic component comprising a metal or metal ion and an organic component comprising an organic radical to which the metallic component is bound. The metallic components of each of the antimicrobial additives of an MFMB together constitute the metallic components of the MFMB. The organic components of each of the antimicrobial additives of an MFMB together constitute the organic components of the MFMB.

For purposes of the present invention, the term "organometallic additive" refers to a compound including a metal bound to an organic radical, where the metal species has a valence state of +1, +2, +3, etc.

For purposes of the present invention, the term "room temperature" refers to a temperature of from about 20° C. to about 25° C.

For purposes of the present invention, the term "sparingly soluble in water" refers to a substance having a solubility of 0.1 g per 100 ml of water to 1 g per 100 ml of water. Unless specified otherwise, the term "sparingly soluble" and "sparingly soluble in water" are used interchangeably in the description of the invention below to refer to substances that are sparingly soluble in water.

For purposes of the present invention, the term "water insoluble" refers to a substance that has a solubility of less than 0.1 g per 100 ml of water.

DESCRIPTION

Because material surfaces can become contaminated with disease causing agents, there is a need for materials with anti-bacterial, anti-fungal, anti-mold, anti-protozoan, anti-algae, anti-yeast, etc. functionality; these are generally referred to as antimicrobials. Liquid material systems such as but not limited to liquid systems made from organic materials, inorganic materials, or organic-inorganic materials blends are ubiquitous in the environment, and if made with antimicrobial disease reducing agents would play a valuable role in producing a healthier environment when applied to material surfaces.

Three types of antimicrobial additives have commonly been used in producing antimicrobial liquids: (1) nanoscale metal particles, (2) metal aluminosilicates, and (3) organic compounds. But existing antimicrobial additives have limitations such as: (1) wearing out from repeated handling, washing, or scrubbing of surface applied materials; (2) rending bulk material non-recyclable, (3) not conferring significant antimicrobial resistance; (4) having a narrow range of effectiveness against antimicrobial agents, (5) the additives being potentially toxic to humans when present in a liquid in a sufficient concentration to be toxic to viruses and molds; and (6) the presence of the additive in a liquid product may require modifications to how the liquid product is manufactured. Particular types of antimicrobial additives for liquids have additional issues.

For example, with respect to metal and aluminosilicate antimicrobial additives, mixing these types of additives with liquids also can lead to wearing out of mixing tools, leading to more frequent tool replacements. Metal and aluminosilicate antimicrobial additives are also costly and may require novel chemical moieties as surface ligands to help disperse and keep the particles of the additives from settling or agglomerating in the organic host liquid.

Organic antimicrobial additives in many cases cannot be readily incorporated with most liquid organic or inorganic materials since these additives are often: (a) chemically aggressive and inhibit the reaction processes of many organic liquid systems and (b) degrade the mechanical, thermal, and optical properties of many organic liquid systems.

In one embodiment, the present invention provides a multifunctional metal blend (MFMB) organometallic additives that form an antimicrobial-resistant liquid material system (e.g., the MFMB organometallic additives may be blended, dispersed, dissolved, distributed, mixed, suspended, scattered, etc.) with an organic host liquid and are distributed homogeneously throughout the organic host liquid. The liquid material systems with multifunctional organometallic additives have enhanced rheological properties (e.g. surface energy) in the liquid state to optimally wet the substrate and superior mechanical properties (e.g. adhesion) in the semi-solid or dried solid state to adhere to the substrate. In addition, chemical bonding such as but not limited to hydrogen bonding may also enhance the mechanical properties when the liquid changes phase to the semi-solid or solid state. The MFMB does not yield discrete metal particles in the liquid system but is instead a liquid solution of organometallic additives in an organic host liquid. Also, the organic host liquid may demonstrate the physical properties of a solid material, a liquid material, or a material having both solid-like and liquid-like physical properties after it is dispersed onto a surface.

Previously, organometallic compounds that are insoluble or sparingly soluble in water have not been considered as antimicrobial additives. However, it has now been discovered that such organometallic compounds can impart antimicrobial functionality to a myriad of organic liquid and inorganic/organic blend liquid systems. Furthermore, literature test data on MFMB material systems shows that the LD50 (median lethal dose) level is relatively low, indicating that health impacts (e.g., toxicity) are expected to be low for at least some antimicrobial compounds.

In one embodiment, the present invention provides an antimicrobial organometallic additive that is dispersed in an organic host liquid to thereby form an antimicrobial liquid material system. The antimicrobial organometallic additive comprises an antimicrobial metal (e.g., copper, silver, zinc, etc.) bound to an organic radical.

In one embodiment, the invention works by integrating an MFMB system that is compatible with a variety of organic host liquids. Uniquely, the MFMB system enables organic liquid processing using conventional manufacturing equipment without the need for additional or secondary equipment to fabricate MFMB organic liquid systems.

In one embodiment, the present invention provides an antimicrobial liquid system that is deposited on a substrate as a coating to provide antimicrobial protection to the substrate. Such a coating may also act as a surface protector and barrier. The liquid material system coatings of the present invention may be used on a variety of substrates such as substrates that are plastics, polymers, rubbers, metals, alloys, fiberglass, cellulose-based materials such as: woods, plywood, pressed woods, papers, cardboards, etc., cloth, leather, fabric, silk, wool, etc. The substrates may be various types of items such as: carts, hospital gurneys, desks, chairs, car seats, metal gratings, shelving (e.g., refrigerator, produce, dairy, candy, and health care products), filters, filter elements (paper, polymer, etc.), sinks (metal, porcelain, plastic, etc.), countertops (laminates, metallic, granite, stone, concrete, etc.), flooring (wood, sealed wood, vinyl, concrete, ceramic tile, grout, polyurethane, epoxy, etc.), walls (wood, plaster, drywall, plasterboard, gypsum board, cement board, concrete, ceramic tile, grout, etc.), ceilings (wood, plaster, drywall plasterboard, gypsum board, cement board, concrete, ceramic tile, grout, etc.), hardware (door handles, door knobs, drawer handles, strike plates, towel rods, light switch plates, outlet plates, etc.), thread, rope, (for example, cotton, silk, wool, polymer, etc.), painted surfaces (latex paint, enamel paint, varnish, etc.), inks, printing inks, and corrugated metal such as used for architectural wall finishing, etc. Liquid material system coatings of the present invention may also be coated on host substrates such as gratings, animal cages, livestock fencing, animal feeding containers (bowls, troughs, plates, dispensers, etc.), animal waste containers (for example litter boxes, etc.), filters (for example, water, air, etc.), synthetic and natural architectural wall finishing, privacy walls and curtains (in bathrooms, hospital rooms, etc.), hand dryers, hand rails and escalator guard rails, and fiberglass surfaces (for example on boats, insulation products, etc.). A liquid material system coating of the present invention may be transparent, translucent or opaque and may be colored with dyes (e.g., organic polymers, inorganic suspensions).

Figure 1:
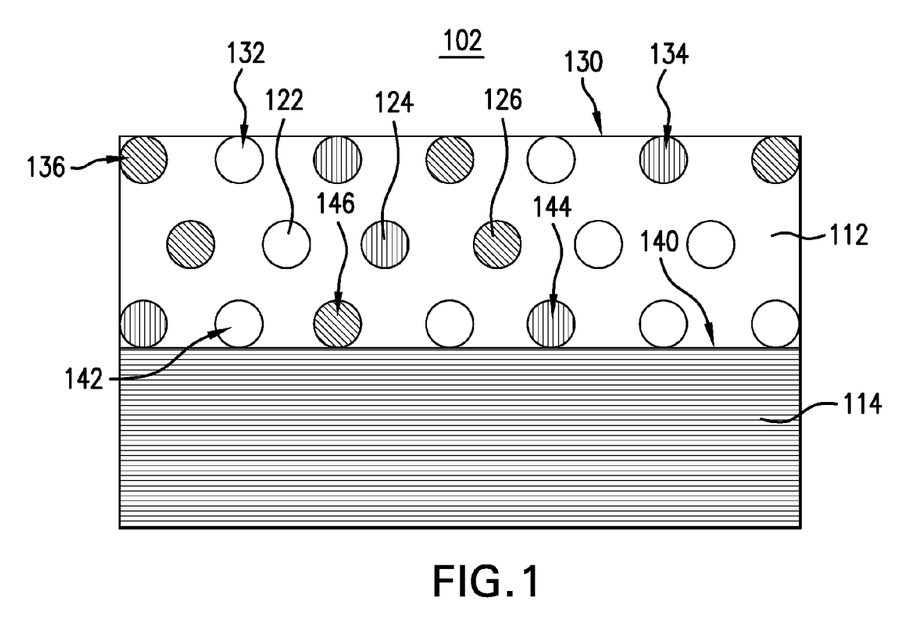
FIG. 1 is a schematic drawing of a an organic liquid material system film deposited on a substrate according to one embodiment of the present invention.

FIG. 1 shows a coated substrate 102 according to one embodiment of the present invention. Coated substrate 102 comprises a liquid material system film 112 coated on a substrate 114. Liquid material system film 112 contains a blend of three different antimicrobial organometallic additives, i.e., antimicrobial organometallic additives 122, 124 and 126, dispersed uniformly or at least substantially uniformly throughout an organic host liquid of liquid material system film 112. Antimicrobial organometallic additives 122, 124 and 126 are present at a surface 130 of liquid material system film 112, as shown by arrows 132, 134 and 136, respectively, and at an interface 140 between liquid material system film 112 and substrate 114, as shown by arrows 142, 144 and 146, respectively. Liquid material system film 112 is chemically and/or mechanically bonded to the substrate 114 at interface 140.

The liquid component of the liquid material system film may be either organic or inorganic.

The liquid material system film may remain a liquid or undergo a phase change to the semi-solid or solid state.

In one embodiment, the liquid material system film thickness is less than about 1 mm thick.

Although three antimicrobial organometallic additives are shown in coated substrate of FIG. 1, there may be one, two, three, four or more antimicrobial organometallic additives in a polymer coating of the present invention. The antimicrobial organometallic additives may be of the same chemistry or they may be of different chemistries.

The substrate on which an organic liquid material system film is coated may be a metal such as aluminum, titanium, copper, brass, bronze, nickel, pewter, silver, gold, stainless steel, carbon steel, steel, molybdenum, Inconel, alloys of these metals, etc., a ceramic such as aluminum oxide (sapphire), ceramic tile, glass (borosilicate, soda-lime-silicate, quartz), granite, marble, porcelain, etc., a plastic such as a vinyl polymer, polycarbonate, polyethylene, polypropylene, polyethylene naphthalate (PEN), polyethylene teraphthalate (PET), wax (paraffin), etc., fabric such as cotton, polymer blend, wool, silk, leather or blends of these threads, concrete, wood, painted surfaces, paper, fiberglass, or any other type of suitable substrate material.

Furthermore, because liquid material systems of the present invention are liquids, they may be applied to a substrate by spraying from an aerosol container, a pump spray container, a pressurized gas system (e.g., spray painter other than an aerosol container) or by mechanical application (pouring and wiping) such as but not limited by cloth, textile, paper towel, brush, roller, etc. Liquid material systems of the present invention present invention may also be applied as printing inks using conventional printing presses, stamps, etc.

In one embodiment of the present invention, the one or more antimicrobial organometallic additives of a multifunctional metal blend (MFMB) impart antimicrobial functionality to the surface of a substrate to which a liquid material system of the present invention has been applied when the liquid material system changes phase to a semi-solid or solid state.

Figure 2:
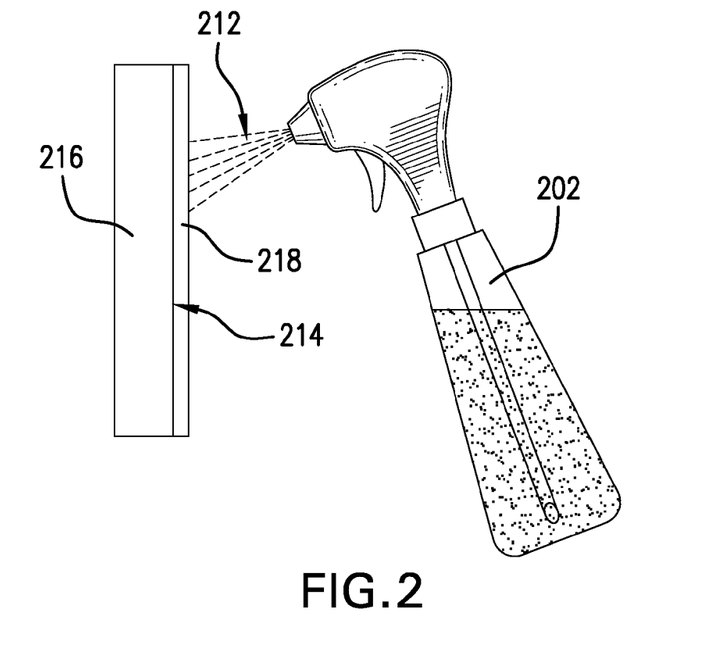
FIG. 2 is a schematic drawing of a liquid material system of the present invention being applied as an antimicrobial coating on a substrate using a pump spray system.

FIG. 2 depicts a pump spray deposition system 202, such as a spray bottle, for spraying a liquid material system 212 onto a surface 214 of a substrate 216 to thereby form antimicrobial coating 218 according to one embodiment of the present invention. Antimicrobial coating 218 may dry to a semi-solid or solid state. Antimicrobial coating 218 may be wiped to remove excess liquid. Pump spray deposition system 202 is a manually operated system that relies on a user pumping pump spray deposition system 202 to thereby generate pressurized air to spray liquid material system 212 onto surface 214 of substrate 216.

Figure 3:
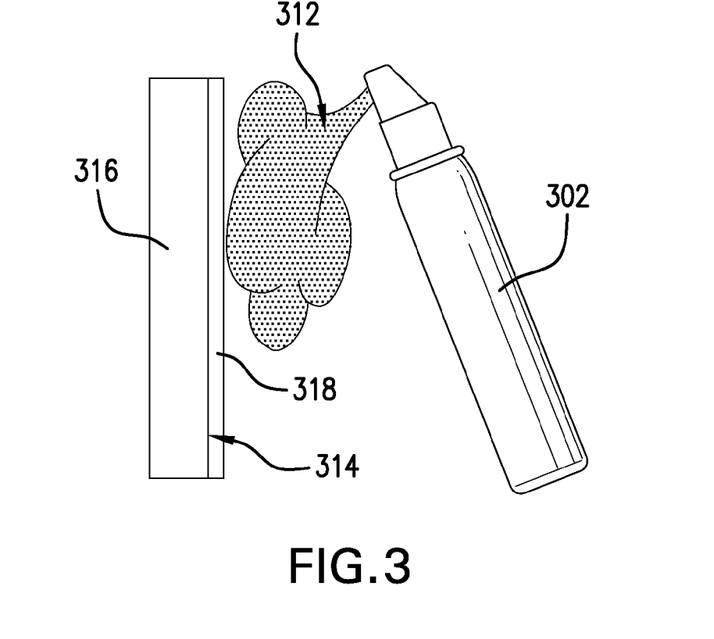
FIG. 3 is a schematic drawing of a liquid material system of the present invention being applied as an antimicrobial coating on a substrate using an aerosol spray system.

FIG. 3 depicts an aerosol spray deposition system 302, such as an aerosol spray bottle, for spraying a liquid material system 312 onto a surface 314 of a substrate 316 to thereby form an antimicrobial coating 318 according to one embodiment of the present invention. Antimicrobial coating 318 may dry to a semi-solid or solid state. Antimicrobial coating 318 may be wiped to remove excess liquid. Aerosol spray deposition system 302 is a pressurized gas assisted or propellant driven system for spraying a liquid material system 312 onto a surface 314 of a substrate 316.

Metals for the metallic component of antimicrobial organometallic additives of the present invention may be selected based on required functionality (e.g. anti-bacterial, anti-fungal, anti-mold, etc.) and can be chosen from the categories of transition metals, post-transition metals, metalloids, lanthanides, actinides, rare earth metals, alkaline earth metals, and alkali metals. A single MFMB system or multiple MFMB systems can be used to produce a broad spectrum of antimicrobial organic liquid products with designed efficacies against single or multiple pathogen agents.

Metals that may be used as the metallic component of antimicrobial organometallic additives of the present invention include, but are not limited to: copper (Cu), silver (Ag), zinc (Zn), gold (Au), iridium (Ir), palladium (Pd), platinum (Pt), iron (Fe), nickel (Ni), cobalt (Co), niobium (Nb), ruthenium (Ru), rhodium (Rh), tellurium (Te), antimony (Sb), bismuth (Bi), tin (Sn), gallium (Ga), indium (In), titanium (Ti), vanadium (V), chromium, (Cr), manganese (Mn), molybdenum (Mo), tungsten (W), tantalum (Ta), hafnium (Hf), zirconium (Zr), scandium (Sc), and yttrium (Y).

Another class of metals that may be used as the metallic component of antimicrobial organometallic additives of the present invention include, but are not limited to alkali and alkali earth metal and similar elements from the left-side of the Periodic Table including, but limited to: lithium (Li), sodium (Na), potassium (K), rubidium (Rb) cesium (Cs), beryllium (Be), magnesium (Mg), calcium (Ca), strontium (Sr), and barium (Ba).

In one embodiment of the present invention, the water insoluble antimicrobial organometallic additives may comprise a long-chain fatty acid group as their organic component. Such compounds include, metal stearates and mixtures thereof. Suitable metal stearates that provide antimicrobial activity when dispersed in an organic host liquid include, silver stearate, copper stearate, zinc stearate, etc., and mixtures thereof. One advantage of using water insoluble antimicrobial organometallic additives having a long-chain fatty acid group as their organic component is that they should provide long-lasting antimicrobial activity to a liquid material system comprising an organic host liquid, even when the liquid material system is exposed to moisture or immersed in water. The water insolubility of such additives and the presence of the long-chain fatty acid group should cause such additives to stay bound and/or complexed in the organic host liquid and not leach into the moisture or water.

This is different than that for water soluble antimicrobial organometallic additives, for example, acetate based systems.

In metal-zeolite-based antimicrobial additives, the metal ion may be released from the zeolite when moisture or water is present, even though the zeolite itself is not water soluble.

Suitable organic host liquids include alcohols, naturally occurring organic liquids and petroleum distillates. Alcohols include but are not limited to methanol, ethanol, butanol, isopropyl alcohol, etc. Naturally occurring organic liquids such as but not limited to turpentine, vegetable oils (e.g., corn oil, canola oil, cotton seed oil, peanut oil, soy oil, rapeseed oil, olive oil, etc.), tung oil, mineral spirits, mineral oil, hydrocarbon liquids, wax, paraffin, biodiesel, etc. Petroleum distillates such as but not limited to turpentine, methyl ethyl ketone (MEK), paint thinner, mineral spirits, mineral oil, hydrocarbon liquids, proprietary organic blends in commercial products such as but not limited to Endust® (containing for example, water, mineral oil, isoparaffin, hexoxyethanol, sorbitan oleate, ethoxylated alcohol, and fragrances) manufactured by Nakoma Products, Pledge® (containing for example, white mineral oil, dimethicone, D Limonene, polyglyceryl oleate, fragrances and dyes) manufactured by SC Johnson, etc., wax, paraffin, benzene, gasoline, kerosene, biodiesel, etc.

In one embodiment of the present invention, an organic host liquid may be the organic dispersed phase of an emulsion. In such an embodiment the organic host liquid is dispersed in a continuous phase of an inorganic liquid such as water, ammonia, etc. The organic host liquid in the dispersed phase may comprise polymer microparticles. Examples of such dispersions of polymer microparticles are natural and synthetic latexes. The organic host liquid may be a single polymer, a polymer blend, a copolymer, or a copolymer blend. The dispersed organic host liquid may contain polymers (such as but not limited to wax, paraffin, polydimethylsiloxane emulsion, acrylics, silicones, 1-part epoxies, 2-part epoxies, etc.) that may solidify and form a film or coating that incorporates the MFMB on a substrate on which the film or coating resides.

Figure 4:
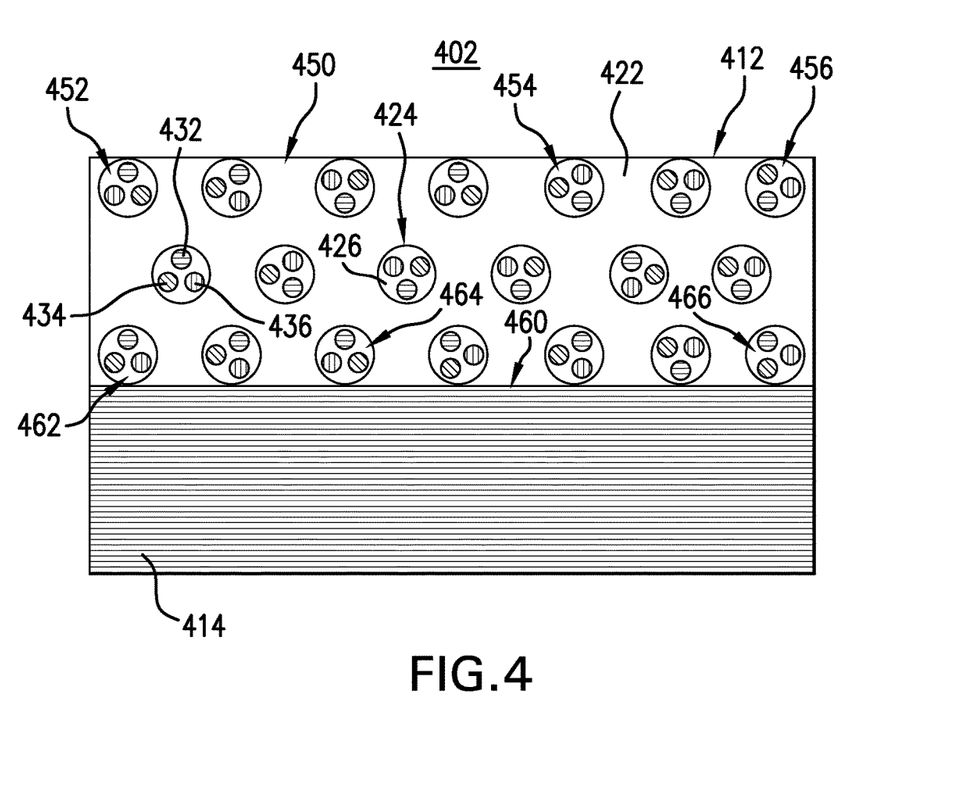
FIG. 4 is a schematic drawing of an organic dispersed liquid material product deposited on a substrate according to one embodiment of the present invention.

FIG. 4 shows a coated substrate 402 according to one embodiment of the present invention. Coated substrate 402 comprises dispersed liquid material product film 412 coated on a substrate 414. Dispersed liquid material product film 412 comprises a continuous phase of an inorganic liquid 422 in which there is dispersed droplets 424 of a dispersed phase, i.e., a dispersed liquid material system, comprising an organic host liquid 426. Each droplet 424 has dispersed therein a blend of three different antimicrobial organometallic additives, i.e., antimicrobial organometallic additives 432, 434 and 436. Droplets 424 are present at a surface 450 of dispersed liquid material product film 412, as shown by arrows 452, 454 and 456, and at an interface 460 between dispersed liquid material product film 412 and substrate 414, as shown by arrows 462, 464 and 466, respectively. Dispersed liquid material product film 412 is chemically and/or mechanically bonded to the substrate 414 at interface 460. In FIG. 4, organic host liquid 426 is dispersed throughout inorganic liquid 422.

Although a blend of three different antimicrobial additives are shown dispersed in the organic host liquid of FIG. 4, one, two, three, four or more different antimicrobial additives may be dispersed in a dispersed liquid material system of the present invention and the different antimicrobial additives may be present in any ratio with respect to each other.

In one embodiment of the present invention, a dispersed liquid material system is about 0.01% to about 5% by volume of the total volume of a dispersed liquid material product of the present invention, i.e., the dispersed liquid material system comprises about 0.01% to about 5% by volume of the total volume of the dispersed liquid material system and the inorganic liquid combined. In one embodiment of the present invention, a dispersed liquid material system is about 0.1% to about 5% by volume of the total volume of a dispersed liquid material product of the present invention, i.e., the dispersed liquid material system comprises about 0.1% to about 5% by volume of the total volume of the dispersed liquid material system and the inorganic liquid combined. In one embodiment of the present invention, the dispersed liquid material system is about 1% to about 3% by volume of the total volume of a dispersed liquid material product of the present invention, i.e., the dispersed liquid material system comprises about 1% to about 3% by volume of the total volume of the dispersed liquid material system and the inorganic liquid combined.

The organic host liquid of the present invention may be formulated so that when the liquid material system changes phase to a semi-solid or solid state, the liquid material system will achieve specific materials properties e.g. optical (clarity, refractive index, color), mechanical (glass transition temperature, coefficient of thermal expansion, elastic and shear modulus, toughness, adhesion, surface roughness), rheological (viscosity, melt flow index, surface energy), electrical (dielectric strength) and anti-microbial efficacy as required for optimal end product performance. During processing the organometallic additive of the organometallic component of a liquid material system may be converted to an organometallic oxide.

In one embodiment, the present invention works by integrating an MFMB system that is incompatible with a variety of inorganic liquids using surfactants and emulsifying agents (emulsifier)s that act as organic host liquids that are simultaneously soluble in the inorganic liquid and can dissolve and are miscible with the MFMB. With at least some antimicrobial organometallic additives of the present invention, the addition of surfactants and emulsifiers allow for greater concentrations of antimicrobial organometallic additives to be used, greater efficacy of the antimicrobial organometallic additive for a given concentration of additive and for greater dispersion of a dispersed organic host liquid and the antimicrobial organometallic additives dispersed in the organic host liquid. Uniquely the MFMB system enables inorganic liquid material systems processing and organic liquid materials system processing using conventional manufacturing equipment. The organic host liquids may contain polymers (such as but not limited to wax, paraffin, polydimethylsiloxane emulsion, acrylics, silicones, 1-part epoxies, 2-part epoxies, etc.) that may solidify and form a film on the substrate that incorporates the MFMB.

Examples of surfactants that may be used in embodiments of the present application include: sorbitan oleate, ethoxylated alcohol, etc.

In one embodiment, the present invention provides uniformly dispersed anti-microbial functionality in a variety of host matrix organic liquid materials systems and inorganic liquid material systems enabling a broad range of deposition systems to apply antimicrobial films and coatings to numerous substrate systems that have various from factors and three-dimensional geometries.

In one embodiment, the antimicrobial additives of the present invention may be organometallic polymers that when dispersed throughout an organic host liquid provides an antimicrobial functionality to the resulting organic liquid material system. The metals in the organometallic polymers may have various electronic structures, for example valence structures of +1, +2, etc. The organometallic polymers may be hydrocarbon based chemical moieties chemically bonded to metals such as silver (Ag), copper (Cu), and zinc (Zn). The polymers can be from families of acetates, stearates, laureates, oleates, abietates, etc., essentially long-chain polymers with a metal atom species, e.g., metallic salts, fatty acids, etc. The MFMB organic chemical structure provides for its enhanced miscibility or dispersion throughout the organic host liquid system. Metallic polymer systems based on silicon chemistries (i.e., silicone-metallic) which exhibit similar metal silicone hybrid structures are also expected to impart antimicrobial functionality to an organic host liquid. Examples of silicone based products include but are not limited to silicone sealants, silicone adhesives, etc.

In one embodiment of the present invention, the antimicrobial organometallic additives may be water insoluble or sparingly soluble in water. A single water insoluble or sparingly insoluble antimicrobial organometallic additive may be employed or mixtures of water insoluble and/or sparingly soluble antimicrobial organometallic additives may be employed.

In one embodiment of the present invention, one or more antimicrobial organometallic additives dispersed in an organic host liquid that is in turn dispersed throughout an inorganic liquid (such as a water, ammonia, etc.) and provide an antimicrobial functionality to the resulting inorganic liquid dispersed system. The inorganic liquid dispersed system may contain additional organic liquids and/or surfactants that enable dissolution of the organometallic polymers so that they may be readily dispersed throughout the inorganic liquid while maintaining their antimicrobial functionality.

In one embodiment of the present invention, the organometallic additives of the liquid material systems are not highly water soluble so that the antimicrobial agent will not leach from the organic liquid material system host when the liquid changes phase to the semi-solid or solid state on a substrate. This is important in products that are in contact with water and food products and medical products, since the antimicrobial agent will have low leachability.

In one embodiment of the present invention, an MFMB organometallic additive may be comprised of a metal such as but not limited to copper (Cu), silver (Ag), gold (Au), iridium (Ir), palladium (Pd), platinum (Pt), iron (Fe), nickel (Ni), cobalt (Co), zinc (Zn), niobium (Nb), ruthenium (Ru), rhodium (Rh), tellurium (Te), antimony (Sb), bismuth (Bi), tin (Sn), gallium (Ga), indium (In), titanium (Ti), vanadium (V), chromium, (Cr), manganese (Mn), molybdenum (Mo), tungsten (W), tantalum (Ta), hafnium (Hf), zirconium (Zr), scandium (Sc), and yttrium (Y) and The inorganic host liquid material system is comprised of at least one of the following, an inorganic host liquid material (e.g. water, ammonia, etc.) that may contain organic liquid materials and or surfactants which are simultaneously soluble/compatible with the inorganic host and can dissolve and are miscible with the MFMB such as materials used in organic liquid material systems. The inorganic host liquid material systems may contain polymers (such as but not limited to wax, paraffin, polydimethylsiloxane emulsion, acrylics, silicones, 1-part epoxies, 2-part epoxies, etc.) that may change phase and form a film or coating that incorporates the MFMB on the substrate on which the film or coating resides. In some embodiments, the film or coating may also remain as a liquid.

An antimicrobial organometallic additive of the present invention may include an organic component that is straight chained, branched, cyclic, aryl, etc. The antimicrobial organometallic additives of the present invention may include organic components that are: acetates, caproates, caprylates, caprates, laurates, myristates, palmitates, stearates, laureates, oleates, abietates, etc.

In one embodiment of the present invention, the total amount of organometallic additives is no more than about 5% by volume of the total volume of the liquid material system of the present invention. In one embodiment of the present invention, the total amount of organometallic additives is about 0.01% to about 5% by volume of the total volume of the liquid material system of the present invention. In one embodiment of the present invention, the total amount of organometallic additives is about 1% to about 3% by volume of the total volume of the liquid material system of the present invention.

In one embodiment of the present invention, an antimicrobial liquid can be made by dispersing an antimicrobial material comprising and inorganic non-metal component such as but not limited to fluorine (F), chorine (Cl), bromine (Br), iodine (I), sulfur (S), selenium (Se), and phosphorus (P) and an organic component (straight chain, or having branches or rings) comprised of but not limited to acetates, caproates, caprylates, caprates, laurates, myristates, palmitates, stearates, laureates, oleates, abietates, etc.

In one embodiment of the present invention the organic host liquid may be an organic liquid or mixtures of organic liquids comprised of at least one of the following: (a) alcohols including but are not limited to methanol, ethanol, butanol, -isopropyl alcohol, etc., (b) naturally-occurring organic liquids such as: turpentine, vegetable oils (e.g., corn oil, canola oil, cotton seed oil, peanut oil, soy oil, rapeseed oil, olive oil, etc.), tung oil, mineral spirits, mineral oil, hydrocarbon liquids, wax, paraffin, biodiesel, etc., (c) petroleum distillates such as but not limited to turpentine, methyl ethyl ketone (MEK), paint thinner, mineral spirits, mineral oil, hydrocarbon liquids, proprietary organic blends in commercial products (such as but not limited to Endust®, Pledge®, etc.), wax, paraffin, benzene, gasoline, kerosene, biodiesel, etc.

In one embodiment of the present invention an organic host liquid may have dispersed therein non-polymeric carbon, such as graphite, graphene, single-walled and multi-walled carbon nanotubes and other types of fullerenes.

In one embodiment, the organic host liquid may be an organic host liquid that is dispersed as an emulsion of polymer microparticles in an aqueous medium such as, but not limited to natural and synthetic latexes. In one embodiment of the present invention, the one or more antimicrobial organometallic additives of a multifunctional metal blend (MFMB) impart antimicrobial functionality to the surface of a substrate to which a liquid material system of the present invention has been applied when inorganic host liquid evaporates leaving behind a semi-solid film, solid film or coating.

In one embodiment of the present invention the organic host liquid may be an organic liquid that is a single polymer, a polymer blend, a copolymer, or a copolymer blend. An organic host liquid of the present invention may have dispersed therein polymers (such as but not limited to wax, paraffin, polydimethylsiloxane emulsion, acrylics, silicones, 1-part epoxies, 2-part epoxies, etc.) that may solidify and form a film or coating that incorporates the MFMB on the substrate on which the film or coating resides. In some embodiments, the film or coating may also remain as a liquid.

According to one embodiment, an organic host liquid of the present invention may comprise an inorganic liquid such as water, ammonia, etc., that contain or in which there are dispersed other additives such as organic liquid materials and/or surfactants that are soluble/compatible with the inorganic host and can dissolve and/or are miscible with each of the antimicrobial organometallic additives of an MFMB. An inorganic host liquid may have dispersed therein additives that are polymers. These polymers may be polymers such as wax, polydimethylsiloxane emulsions, polydimethylsiloxane emulsions, acrylics, silicones, 1-part epoxies, 2-part epoxies, etc., that may solidify and form a film or coating that incorporates the MFMB on the substrate on which the film or coating resides.

In one embodiment of the present invention the organic host liquid may be comprised of a stable dispersion (emulsion) of polymer microparticles in an aqueous medium. The antimicrobial organometallic additive or mixture of organometallic additives may be dispersed in the polymer microparticles that are in turn dispersed in the aqueous medium. Examples of such dispersions include emulsions such as, but not limited to natural and synthetic latexes.

An organic or inorganic host liquid of the present invention may contain fluorine (F), chorine (Cl), bromine (Br), iodine (I), sulfur (S), selenium (Se), and phosphorus (P).

A substrate of the present invention may take many forms such as but not limited to flat, curved, dimpled, textured, three-dimensional, etc. The substrates of the present invention may be made of materials such as but not limited to: Formica® (a plastic laminate), laminates, wood, painted surfaces, decoratively finished surfaces, wallpaper, tile, metals (aluminum, brass, stainless steel, nickel, titanium, pewter, silver, and their alloys, etc.), glass, ceramic, concrete, plaster, grout, fabric, textile, leather, vinyl, plastics, polymers (thermoplastics, thermosets, polypropylene, polyester, polyethylene, polyurethane, polyvinyl chloride (PVC), polystyrene, acrylics, polymethyl methacrylate (PMMA), acrylonitrile butadiene styrene (ABS), polycarbonate, 1-part epoxies, 2-part epoxies, etc.), nylon, Teflon, rubber, silicone, granite, marble, quartz, porcelain, paper, cardboard, cellulose products, etc. In some cases the substrate may be living plants, trees, bushes, flowers, vegetables, fruits, etc., so that the antimicrobial functionality of the organic liquid material system or the inorganic liquid material system may protect the substrate from microbial, viral, fungal, etc., infestations.

In one embodiment of the present invention, the organic host liquid may comprise a polyurethane. The organic host liquid may be a one-part polyurethane liquid polymer or a two-part polyurethane liquid polymer. The polyurethane organic host liquid may be air cured, thermally cured, or UV-radiation cured.

In one embodiment a liquid material system coating may be transparent has a refractive index of at least 1.1 at 633 nm with optical transmission of >90% from 375 to 600 nm. In one embodiment of the present invention, a coating may be less than 1 mm thick.

The antimicrobial organometallic additive in a liquid material system of the present invention may be at various ratios with respect to each other. For example, when a blend of three antimicrobial organometallic additives are dispersed in a liquid host of the present invention, the ratio of the antimicrobial organometallic additives may be 1:1:1, 1:2:1, 2:3:4, or any other suitable ratio.

In one embodiment, the antimicrobial organometallic additives may be a majority of the metallic species present in a liquid material system of the present invention. In some embodiments of the present invention there may be low levels of metals or metal ions present from other additives (e.g., UV protectors, colorants, etc.) dispersed throughout a liquid host of the liquid material system. In some embodiments of the present invention, the antimicrobial organometallic additives may be the only metallic species present in a polymer host matrix of a polymer product of the present invention.

In one embodiment, the present invention provides a liquid product having antimicrobial activity that may be made by mixing one or more antimicrobial organometallic additives of the present invention with host organic liquid at room temperature.

The present invention will now be described by way of example.

EXAMPLES

Several compositions were prepared to demonstrate the antimicrobial efficacy of MFMB materials in various organic liquid material systems and inorganic liquid material systems. Antimicrobial efficacy was demonstrated by testing samples using the JIS Z 2801 test protocol. Testing was conducted by a third party laboratory, Antimicrobial Test Laboratories (ATL), 1304 W. Industrial Blvd, Round Rock Tex. 78681.

Example 1

MFMB material containing copper stearate was added to an organic host liquid. The organic host liquid was comprised of water, mineral oil, isoparaffin, hexoxyethanol, sorbitan oleate, ethoxylated alcohol, and fragrances (Endust® Multi-Surface Dusting Spray manufactured by Nakoma Products), a commercial material system used to provide protective, non-antimicrobial materials to a substrate surface. About 200 ml of the organic host liquid was mixed with 2 ml of copper stearate to produce a 1% by volume blend. This organic liquid material system sample was placed into a pump-spray container and sprayed onto a Formica® substrate and wiped dry per the manufacturer's directions. The sample was tested by ATL and 99.999996% reduction in Colony Forming Units (CFU) was observed.

This demonstrates that copper stearate can be added to organic liquid material systems and produce antimicrobial functionality on the substrate surface.

Example 2

An MFMB material containing copper stearate was added to Samaritan™ Protective Clearcoat, a commercial liquid comprising water and dimethylsiloxane used to provide protection to hard substrate surfaces. About 200 ml of Samaritan™ liquid was mixed with 0.6 ml of copper stearate to produce a 0.3% by volume blend. This inorganic liquid material system sample was placed into a pump-spray container and sprayed onto a Formica® substrate and wiped dry per the manufacturer's directions. The sample was tested by ATL and 99.996% reduction in Colony Forming Units (CFU) was observed. The copper stearate was added to the Samaritan™ Protective Clearcoat with no surfactants or emulsifiers. The dimethlysiloxane was sufficient to dissolve some of the copper stearate.

Example 3

Examples of metals that may be used as the metallic component of an MFMB according to one embodiment of the present invention include the antimicrobial metals copper, silver and zinc. In an MFMB the antimicrobial metal has a non-zero valence state, e.g., +1, +2, etc. Examples of organic radicals that may be used as the organic component of an MFMB include, but are not limited to acetates, caproates, caprylates, caprates, laurates, myristates, palmitates, stearates, oleates, and abietates. Furthermore the organic radical may be a straight chain, a branched, cyclic, aryl, etc., organic radical. The chemical moieties comprising the branches and rings of the organic radical may impart enhanced chemical, rheological, mechanical, or antimicrobial properties. Examples of some MFMB materials according to one embodiment of the present invention are shown in Table 1.

TABLE 1

Examples of MFMB material systems

| Name | Chemical formula | CAS Number | Comments |
|---|---|---|---|
| Copper (II) Acetate | $C_4H_6CuO_4$ | 142-71-2 | |
| Silver (I) Acetate | $C_2H_3Ag\,O_2$ | 563-63-3 | Used in antismoking lozenges (2.5 mg) |
| Zinc Acetate | $C_4H_{10}O_6Zn$ | 557-34-6 | Food additive number E650 |
| Copper (II) Stearate | $C_{36}H_{70}CuO_4$ | 660-60-6 | |
| Silver Stearate | $C_{18}H_{35}AgO_2$ | 3507-99-1 | |
| Zinc Stearate | $C_{36}H_{70}O_4Zn$ | 557-05-1 | |
| Copper Laurate | $C_{24}H_{46}CuO_4$ | 19179-44-3 | |
| Silver Laurate | $C_{12}H_{23}AgO_2$ | 18268-45-6 | |
| Zinc Laurate | $C_{24}H_{46}O_4Zn$ | 2452-01-9 | |
| Copper (II) Oleate | $C_{36}H_{66}CuO_4$ | 1120-44-1 | Fungicide |
| Silver Oleate | $C_{36}H_{66}O_4Ag$ | | |
| Zinc Oleate | $C_{36}H_{66}O_4Zn$ | 557-07-3 | |
| Copper Abietate | $C_{40}H_{58}O_4Cu$ | 10248-55-2 | Fungicide |
| Silver Abietate | $C_{40}H_{58}O_4Ag$ | | CAS EOPA PC 023301 |
| Zinc Abietate | $C_{40}H_{58}O_4Zn$ | 6798-76-1 | |

This demonstrates that copper stearate can be added to inorganic liquid material systems and produce antimicrobial functionality on the substrate surface.

All documents, patents, journal articles and other materials cited in the present application are incorporated herein by reference.

Having described a particular embodiment of the present invention, it will be apparent that modifications and variations are possible without departing from the scope of the invention as defined in the appended claims. Furthermore, it should be appreciated that all examples provided in the present disclosure, while illustrating a particular embodiment of the invention, are provided as non-limiting examples and are, therefore, not to be taken as limiting the various aspects so illustrated.

While the present invention has been disclosed with references to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims and equivalents thereof.

What is claimed is:

1. A product comprising:
    an inorganic liquid; and
    a dispersed liquid material system including,
        an organic host liquid in the form of droplets dispersed throughout the inorganic liquid, and
        one or more first antimicrobial organometallic additives dispersed throughout each of the droplets of the organic host liquid,
    wherein each of the one or more first antimicrobial organometallic additives is water insoluble or sparingly soluble in water and comprises a long-chain fatty acid group, and
    wherein the organic host liquid is a liquid at room temperature.

2. The product of claim 1, wherein a majority of metallic species in the dispersed liquid material system are in the one or more first antimicrobial organometallic additives.

3. The product of claim 1, wherein the one or more first antimicrobial organometallic additives comprise silver stearate.

4. The product of claim 1, wherein the one or more first antimicrobial organometallic additives comprise copper stearate.

5. The product of claim 1, wherein the one or more first antimicrobial organometallic additives comprise zinc stearate.

6. The product of claim 1, further comprising:
    a mixture of one or more second antimicrobial organometallic additives and the one or more first antimicrobial organometallic additives,
    wherein the one or more first and second antimicrobial organometallic additives are two or more members of the group consisting of the following antimicrobial organometallic additives: silver stearate, copper stearate and zinc stearate.

7. The product of claim 1, wherein the product has a degree of antimicrobial activity of 99% or greater.

8. The product of claim 7, wherein the one or more first antimicrobial organometallic additives together comprise no more than about 5% by volume of the total volume of the dispersed liquid material system.

9. The product of claim 1, wherein the product comprises a coating on a substrate, and wherein the coating comprises the dispersed liquid material system dispersed in the inorganic liquid.

10. The product of claim 1, wherein the dispersed liquid material system comprises about 0.01% to about 5% by volume of the total volume of the dispersed liquid material system and the inorganic liquid combined.

11. The product of claim 1, wherein water comprises a majority of the inorganic liquid.

12. A method comprising:
    dispersing a liquid material system in an inorganic liquid to thereby form a dispersed liquid material product including the dispersed liquid material system dispersed in the inorganic liquid,
    wherein the dispersed liquid material system comprises an organic host liquid in the form of droplets,
    wherein one or more first antimicrobial organometallic additives are dispersed throughout each of the droplets of the organic host liquid,
    wherein the organic host liquid is dispersed throughout the inorganic liquid,
    wherein each of the one or more first antimicrobial organometallic additives is water insoluble or sparingly soluble in water and comprises a long-chain fatty acid group, and
    wherein the organic host liquid is a liquid at room temperature.

13. The method of claim 12, wherein majority of metallic species in the dispersed liquid material system are in the one or more first antimicrobial organometallic additives.

14. The method of claim 12, wherein the one or more first antimicrobial organometallic additives comprise silver stearate.

15. The method of claim 12, wherein the one or more first antimicrobial organometallic additives comprise copper stearate.

16. The method of claim 12, wherein the one or more first antimicrobial organometallic additives comprise zinc stearate.

17. The method of claim 12, further comprising:
a mixture of one or more second antimicrobial organometallic additives and the one or more first antimicrobial organometallic additives,
wherein the one or more first and second antimicrobial organometallic additives are two or more members of the group consisting of the following antimicrobial organometallic additives: silver stearate, copper stearate and zinc stearate.

18. The method of claim 12, wherein the dispersed liquid material product has a degree of antimicrobial activity of 99% or greater.

19. The method of claim 18, wherein the one or more first antimicrobial organometallic additives together comprise no more than about 5% by volume of the dispersed liquid material system.

20. The method of claim 12, wherein the method comprises applying the dispersed liquid material product to a substrate to thereby form a coating on the substrate.

21. The method of claim 12, wherein the dispersed liquid material system comprises about 0.01% to about 5% by volume of the liquid material product.

22. The method of claim 12, wherein water comprises a majority of the inorganic liquid.

23. A product comprising:
a liquid material system including,
an organic host liquid in the form of droplets, and
one or more first antimicrobial organometallic additives dispersed throughout each of the droplets of the organic host liquid,
wherein each of the one or more first antimicrobial organometallic additives is water insoluble or sparingly soluble in water and comprises a long-chain fatty acid group, and
wherein the organic host liquid is a liquid at room temperature.

24. The product of claim 23, wherein a majority of metallic species in the liquid material system are in the one or more first antimicrobial organometallic additives.

25. The product of claim 23, wherein the one or more first antimicrobial organometallic additives comprise silver stearate.

26. The product of claim 23, wherein the one or more first antimicrobial organometallic additives comprise copper stearate.

27. The product of claim 23, wherein the one or more first antimicrobial organometallic additives comprise zinc stearate.

28. The product of claim 23, further comprising:
a mixture of one or more second antimicrobial organometallic additives and the one or more first antimicrobial organometallic additives,
wherein the one or more first and second antimicrobial organometallic additives are two or more members of the group consisting of the following antimicrobial organometallic additives: silver stearate, copper stearate and zinc stearate.

29. The product of claim 23, wherein the product has a degree of antimicrobial activity of 99% or greater.

30. The product of claim 29, wherein the one or more first antimicrobial organometallic additives together comprise no more than about 5% by volume of the liquid material system.

31. The product of claim 23, wherein the product comprises a coating on a substrate, and wherein the liquid material system comprises at least part of the coating.

32. A method comprising:
mixing one or more first antimicrobial organometallic additives with an organic host liquid in the form of droplets to thereby form a liquid material system including the one or more first antimicrobial organometallic additives dispersed throughout each of the droplets of the organic host liquid,
wherein each of the one or more first antimicrobial organometallic additives is water insoluble or sparingly soluble in water and comprises a long-chain fatty acid group, and
wherein the organic host liquid is a liquid at room temperature.

33. The method of claim 32, wherein majority of metallic species in the liquid material system are in the one or more first antimicrobial organometallic additives.

34. The method of claim 32, wherein the one or more first antimicrobial organometallic additives comprise silver stearate.

35. The method of claim 32, wherein the one or more first antimicrobial organometallic additives comprise copper stearate.

36. The method of claim 32, wherein the one or more first antimicrobial organometallic additives comprise zinc stearate.

37. The method of claim 32, further comprising:
a mixture of one or more second antimicrobial organometallic additives and the one or more first antimicrobial organometallic additives,
wherein the one or more first and second antimicrobial organometallic additives are two or more members of the group consisting of the following antimicrobial organometallic additives: silver stearate, copper stearate and zinc stearate.

38. The method of claim 32, wherein the liquid material system has a degree of antimicrobial activity of 99% or greater.

39. The method of claim 38, wherein the one or more first antimicrobial organometallic additives together comprise no more than about 5% by volume of volume of the liquid material system.

40. The method of claim 32, wherein the method comprises applying the liquid material system to a substrate to thereby form a coating on the substrate.

41. The product of claim 1, wherein the organic host liquid is a dispersed phase of an emulsion in the inorganic liquid.

42. The product of claim 1, wherein the total amount of the one or more first antimicrobial organometallic additives is about 0.1% to about 5% by volume of the total volume of the dispersed liquid material system and the inorganic liquid combined.

43. The product of claim 1, wherein the dispersed liquid material system comprises about 1% to about 3% by volume of the total volume of the dispersed liquid material system and the inorganic liquid combined.

44. The product of claim 23, wherein the organic host liquid comprises (i) mineral oil, isoparaffin, hexoxyethanol, sorbitan oleate and ethoxylated alcohol, (ii) white mineral oil, dimethicone, and polyglyceryl oleate, or (iii) at least one selected from turpentine, vegetable oils, tung oil, mineral spirits, mineral oil, hydrocarbon liquids, wax, biodiesel, methyl ethyl ketone (MEK), and paint thinner.

45. The product of claim 23, wherein the organic host liquid comprises polydimethylsiloxane.

46. The product of claim 1, wherein the organic host liquid includes a polyurethane, and said polyurethane is cured thermally or by air or by UV-radiation.

47. The product of claim 1, wherein the dispersed liquid material system includes the one or more first antimicrobial organometallic additives being dispersed throughout each of the droplets of the organic host liquid prior to the organic host liquid being dispersed in the form of droplets throughout the inorganic liquid.

* * * * *